United States Patent [19]

Bos et al.

[11] Patent Number: 4,695,628

[45] Date of Patent: Sep. 22, 1987

[54] PREPARATION OF 6-AMINO-PENICILLANIC ACID-1,1-DIOXIDE

[75] Inventors: Jacobus J. Bos, Gouda; Rinze Cuperus, Pijnacker; Rudolf Wielinga, De Lier, all of Netherlands

[73] Assignee: Gist-Brocades N.V., Delft, Netherlands

[21] Appl. No.: 904,190

[22] Filed: Sep. 5, 1986

[30] Foreign Application Priority Data

Sep. 6, 1985 [EP] European Pat. Off. ........ 85201409.1

[51] Int. Cl.$^4$ ................. C07D 499/02; A61K 31/425
[52] U.S. Cl. .................................... 540/312; 540/310; 540/219
[58] Field of Search ................ 540/312, 310; 514/195

[56] References Cited

U.S. PATENT DOCUMENTS 4,260,598 4/1981 Barth .................................. 514/195

OTHER PUBLICATIONS

Spry, J. Org. Chem., vol. 37, No. 5, pp. 793–795 (1972).
Essery et al., J. Org. Chem., vol. 30, p. 4388 (1965).
Micetich, Synthesis, pp. 264–265, Apr. 1976.

*Primary Examiner*—Nicholas S. Rizzo
*Attorney, Agent, or Firm*—Bierman & Muserlian

[57] ABSTRACT

A process for the preparation of 6-amino-pencillanic acid-1,1-dioxide without protecing either the amino group or the carboxy group during oxidation, by oxidation of 6-amino-penicillanic acid or 6-amino penicillanic acid sulfoxide with an alkali metal permanganate in an aqueous medium.

5 Claims, No Drawings

PREPARATION OF 6-AMINO-PENICILLANIC ACID-1,1-DIOXIDE

STATE OF THE ART

One of today's most well-known and widely used classes of anti-bacterial compounds are the β-lactam antibiotics which have a 2-azeti dinone (β-lactam) ring fused to a thiazolidine ring (penicillins) or a dihydro-1,3-thiazine ring (cephalosporins). Typical examples of penicillins are benzylpenicillin (penicillin G), phenoxymethylpenicillin (penicillin V), ampicillin and amoxycillin. However, certain penicillins are inactive or almost inactive against certain microorganisms, due, it is thought, to the production of a β-lactamase by the microorganism.

β-lactamases are enzymes which cleave the 8-lactam ring of the penicillin leading to decomposition products which do not possess anti-bacterial activity. This is a growing problem in that more bacteria become resistant to penicillins by the acquisition of the ability to produce β-lactamases. However, several new classes of compounds have been discovered which inhibited 5-lactamases and, when used in combination with a penicillin, can increase or enhance the antibacterial activity of the penicillin against the bacteria.

EP-A-0002927 describes the use of 6-amino penicillanic acid-1,1-dioxide and its salts to enhance the antibacterial activity of β-lactam antibiotics. Netherlands Application No. 78-06126 discloses that penicillanic acid-1,1-dioxide and its salt and esters have useful pharmacological properties, for example as effective inhibitors of several types of β-lactamases present in various bacteria. Penicillanic acid-1,1-dioxide can be prepared from 6-amino-penicillanic acid-1,1-dioxide by diazotising the 6-amino-penicillanic acid and subsequently brominating the diazotised compounds, followd by debromination of the brominated products as described in EP-A-0093465 and 0092286 It will be appreciated therefore, that 6-amino-penicillanic acid-1,1-dioxide is a valuable compound.

EP-A-0002927 describes the preparation of 6-amino-penicillanic acid-1,1-dioxide by oxidation of a 6-aminopenillanic acid derivative in which the 6-amino-group and preferably also the 3-carboxyl group have been protected, using an oxidizing agent such as potassium permanganate or 3-chloro-perbenzoic acid followed by removing the protecting groups. This method has the disadvantage therefore, that the 6-amino group and usually also the 3-carboxylic acid group must be protected with protecting groups which must be removed after the oxidation without effecting the ring structure or bringing about other undesired structure changes in the molecule.

The direct oxidation of 6-amino-penicillanic acid into 6-amino-penicillanic acid-1,1-dioxide has not been described in the literature. Previous proposals for oxidation of 6-amino-penicillanic acid have always resulted in the formation of the corresponding sulfoxides. For instance, J. Org. Chem., Vol. 30, p. 4388 (1965) describes the oxidation of 6-amino-penicillanic acid into its sulfoxide using sodium metaperiodate but a yield of only 8% was obtained. J. Org. Chem., Vol. 37, p. 793 (1972) describes the conversion of 6-amino-penicillanic acid into its sulfoxide using ozone and a yield of 95% was reported. Although sulfoxides are generally oxidized to sulfones by an excess of ozone, the further oxidation of 6-amino-penicillanic acid sulfoxide to the sulfone with a large excess of ozone did not occur under these conditions. The oxidation of 6-amino-penicillanic acid into its sulfoxide using peracetic acid has been described in Synthesis 264 (1976) and a yield of 49% was reported.

OBJECTS OF THE INVENTION

It is an object of the invention to provide an improved process for the preparation of 6-amino-penicillanic acid-1,1-dioxide without protection of the amino or carboxyl groups.

This and other objects and advantages of the invention will become obvious from the following detailed description.

THE INVENTION

Surprisingly, it has been found that 6-amino-penicillanic acid can be directly oxidized to 6-amino-penicillanic acid-1-1-dioxide without the need for protection of either the 6-amino-group or the 3-carboxyl group during the oxidation if the oxidation is carried out with a permanganate, for instance potassium or sodium permanganate, in an aqueous medium.

By operating in accordance with the present invention, 6-amino-penicillanic acid-1,1-dioxide can be prepared in a two step synthesis starting from benzylpenicillin (penicillin G) which is the most important starting material for all semi-synthetic penicillin compounds because benzylpenicillin is produced in large amounts by fermentation and can be converted into 6-amino-penicillanic acid in yields over 90%.

In accordance with the present invention, 6-amino-penicillanic acid is dissolved in an aqueous solution, for instance a dilute aqueous solution of sulfuric acid to which optionally a co-solvent can be added, for instance acetonitrile, followed by addition of an aqueous solution of the alkali metal permanganate. It is also possible to add a mixture of alkali metal permanganate in water and aqueous sulfuric acid to a suspension of 6-amino-penicillanic acid in water, or in a mixture of water and an inert organic solvent, for instance acetonitrile. In this case, it is possible to conduct the oxidation under neutral or slightly alkaline conditions, for instance by adjusting the pH to 7 or 8 by addition of ammonia. It is also possible to bring about the oxidation by adding solid 6-amino-penicillanic acid to a mixture of the alkali metal permanganate and sulfuric acid in water or a mixture of water and an inert, water-miscible organic solvent, for instance acetonitrile.

Any excess of permanganate remaining can be removed by methods known in the art, for instance by the addition of sodium-meta-bisulfite. The 6-amino-penicillanic acid-1,1-dioxide can be isolated from the reaction mixture by adjusting the pH to approximately 3.3, at which pH the product crystallizes from the reaction mixture.

According to the above described reaction, it is possible to obtain conversion yields of 85% or more of 6-amino-penicillanic acid into its 1,1-dioxide. The oxidation reaction is carried out at temperature between −10° C. and 20° C., preferably between −10° C. and 0° C.

Instead carrying out the oxidation in the presence of sulfuric acid, it is also possible to use other acids, for instance phosphoric acid. Instead of 6-amino penicillanic acid as starting material, it is also possible to use 6-amino penicillanic acid sulfoxide.

In the following examples there are described several preferred embodiments to illustrate the invention. However, it should be understood that the invention is not intended to be limited to the specific embodiments.

EXAMPLE 1

25 g (116 mmol) of 6-amino-penicillanic acid were suspended in a mixture of 80 ml of water and 120 ml of acetonitrile and the reaction mixture was cooled to −10° C. after which a solution of 24 g (152 mmol) of potassium permanganate and 15 ml of concentrated sulfuric acid in 300 ml of water were added at this temperature over 20 minutes. Excess potassium permanganate was destroyed by addition of a concentrated solution of sodium meta-bisulfite (50%). The pH of the solution was adjusted to 3.2 by addition of ammonia during which addition the 6-amino-penicillanic acid, 1,1-dioxide crystallized. The solid mass was filtered off, washed with water/acetone and dried to obtain 24.4 g of solid mass with a content of 6-amino-penicillanic acid-1,1-dioxide of 89% as determined by HPLC. The yield was therefore 76% and the mother liquid contained another 9%.

EXAMPLE 2

25 g (116 mmol) of 6-amino-penicillanic acid were suspended in a mixture of 80 ml of water and 120 ml of acetonitrile and the reaction mixture was cooed to −8° C., after which the pH of the reaction mixture was adjusted to 8.1 by addition of ammonia. To the reaction mixture, a solution of 23.2 g (147 mmol) of potassium permanganate and 7 ml of 85% phosphoric acid in 100 ml of water was added over 35 minutes while maintaining the temperature at −8° C. and the pH at 7.5 by addition of ammonia. After stirring for 30 minutes at −8° C. at pH 7.5, the mixture was filtered and the pH was adjusted to 4.0 by adding 4N HCl solution. 1 ml of saturated sodium-meta-bisulfite solution was added and the pH was lowered to 3.2 by a further addition of 4N hydrochloric acid. The mixture was stirred at −8° C. for 15 minutes and 6-amino-penicillanic acid-1,1-dioxide crystallized under these conditions. The solid mass was filtered off, washed with water/acetone and dried to obtain 22.5 g of solid mass with a content of 6-amino-penicillanic acid-1,1-dioxide of 92.5% as determined by HPLC and the yield was therefore 73%.

EXAMPLE 3

22.5 g (142 mmol) of potassium permanganate were dissolved in a mixture of 100 ml of 6N aqueous sulfuric acid and 175 ml of water and after the potassium permanganate was dissolved, 200 ml of acetonitrile were added. To this solution, 21.6 g (100 mmol) of solid 6-amino-penicillanic acid were added at −5° C. at such a rate that the temperature did not exceed 0° C., followed by stirring at −5° C. to 0° C., 5 g (26 mmol) of sodium meta-bisulfite were added to the solution, whereafter the pH was adjusted at 3.3 by the addition of ammonia. At this pH, 6-amino-penicillanic acid-1,1-dioxide crystallized and the solid was filtered off and dried to obtain 18.6 g of a solid mass with a content of 6-amino-penicillanic acid-1,1-dioxide of 90% as determined by HPLC which yield was therefore 68%.

EXAMPLE 4

25 g (116 mmol) of 6-amino-penicillanic acid were suspended in a mixture of 80 ml of water and 120 ml of acetonitrile and the reaction mixture was cooled to −5° C., after which the pH of the mixture was adjusted to 7.0 by addition of ammonia. To the reaction mixture, a solution of 21.5 g (136 mmol) of sodium permanganate and 7.5 ml of 85% phosphoric acid in 25 ml of water was added over 60 minutes while maintaining the temperature at −5° C. and the pH at 7.0 by addition of ammonia. After stirring for 30 minutes at −5° C. and a pH of 7.0, the mixture was filtered off. The pH was adjusted to 4.0 by adding 6N $H_2SO_4$ solution, and 1 ml of saturated sodium meta-bisulfite solution was added. The pH was lowered to 3.2 by a further addition of acid and stirred at −5° C. for 15 minutes. The 6-amino-penicillanic acid-1,1-dioxide crystallized under these conditions. The crystals were filtered off, washed and dried to obtain 19.0 g of solid mass with a content of 6-amino-penicillanic acid-1,1-dioxide of 91% as determined by HPLC which yield was therefore 60%.

EXAMPLE 5

In a series of experiments, the reactions of 6-amino-penicillanic acid with various oxidizing agents were carried out to compare with the oxidation with alkali metal permanganate under the conditions as described in the Examples 1 to 4 and the results are summarized in the table.

| | | | HPLC | |
|---|---|---|---|---|
| oxidizing agent | conditions | % 6-APA | % 6-APA sulfoxide | % 6-APA 1,1 dioxide |
| $KHSO_5$ | a | 3 | 46 | — |
| $H_2O_2$ + $ZrOCl_2$ | a | 35 | 20 | — |
| m-chloroperbenzoic acid | a | 23 | 44 | — |
| trifluoroperacetic acid | a | 51 | 22 | — |
| performic acid | a | — | 40 | — |
| sodium perborate | a | 9 | 16 | — |
| sodium dichromate | b | 80 | — | — |
| sodium perborate | b | 29 | 50 | — |
| $H_2O_2$ + $ZrOCl_2$ | b | 15 | 30 | — |
| $H_2O_2$ + $ZrCl_4$ | b | 5 | 81 | — |
| $H_2O_2$ + $ZrOCl_2$ | c | — | — | — |
| m-chloroperbenzoic acid | d | — | 100 | — |
| m-chloroperbenzoic acid/ trifluoroacetic acid | d | — | — | — |
| performic acid | d | 90 | 10 | — | a. 10 g (46 mmol) of 6-amino-penicillanic acid were suspended in water, water-acetone, water-acetonitrile or water-glacial acetic acid and the oxidizing agent (90–150 mmol) was added and stirred at 10° C. to 20° C.
b. 10 g (46 mmol) of 6-amino-penicillanic acid were dissolved in $H_2O/H_2SO_4$ at pH 1.0 and the oxidizing agent (130–150 mmol) was added and stirred at 10° C. to 20° C.
c. 10 g (46 mmol) of 6-amino-penicillanic acid were dissolved in $H_2O$/ammonia or $H_2O$/triethylamine at pH 7 and the oxidizing agent (150 mmol was added and stirred at 15° C.
d. 10 g (46 mmol) of 6-amino-penicillanic acid were suspended in a mixture of $H_2O$/dichloromethane and the phase transfer catalyst tetrabutylammonium hydrogensulfate and the oxidizing agent (92–130 mmol) was added and stirred at 10° C.

EXAMPLE 6

A process was carried out as described in Example 1 with the only difference being that one half of the solution containing potassium permanganate was used, i.e. potassium permanganate (12 g, 76 mmol) and 7.5 ml of concentrated sulfuric acid in 150 ml of water was added to the 25 g of 6-amino-penicillanic acid solution. 19 g of solid mass with a content of penicillanic acid-1,1-dioxide of 49% and of unreacted penicillanic acid of 45% as determined by HPLC, were isolated and the yield was therefore 32%.

EXAMPLE 7

6-amino-penicillanic acid sulfoxide (1-oxide) was prepared from 6-amino-penicillanic acid according to Synthesis, 264 (1976).

26.8 g (116 mmol) of 6-amino-penicillanic acid sulfoxide were suspended in a mixture of 100 ml of water and 100 ml of acetonitrile at room temperature. To the reaction mixture, a solution of 22.5 g (142 mmol) and 75 ml of 6N sulfuric acid in 250 ml of water and 250 ml of acetonitrile were added slowly while maintaining the temperature between $-10°$ C. and $-5°$ C. 100 ml of 15% sodium meta-bisulfite were added to the solution, whereafter the pH was adjusted to 3,5 by the addition of ammonia. The formed crystals were filtered off, washed with water and dried to obtain 16.2 g of a solid mass with a content of penicillanic acid-1,1-dioxide of 90.5% as determined by HPLC which yield was therefore 51%.

Various modifications of the process of the invention may be made without departing from the spirit or scope thereof and it should be understood that the invention is intended to be limited only as defined in the appended claims.

What we claim is:

1. A process for the preparation of 6-amino-penicillanic acid-1,1-dioxide, characterized in that 6-amino-penicillanic acid or 6-amino-penicillanic acid sulfoxide is oxidized with an alkali metal permanganate in an aqueous medium.

2. The process of claim 1 wherein an excess of permanganate is used.

3. The process of claim 1 wherein the permanganate is potassium or sodium permanganate.

4. The process of claim 1 wherein the reaction is carried out between $-10°$ C. and $20°$ C.

5. The process of claim 4 wherein the temperature is $-10°$ C. to $0°$ C.

* * * * *